United States Patent [19]

Anquetil et al.

[11] 4,220,560

[45] Sep. 2, 1980

[54] SPINEL DEHYDROGENATION CATALYST

[75] Inventors: Jean-Pierre Anquetil, de Grand Couronne, France; Michel Deflin, Houston, Tex.; Jean-Claude Clement; Emmanuel E. A. Neel, both of de Grand Couronne, France

[73] Assignee: Shell Oil Company, Houston, Tex.

[21] Appl. No.: 966,450

[22] Filed: Dec. 4, 1978

[30] Foreign Application Priority Data

Dec. 12, 1977 [FR] France .................................. 77 37342

[51] Int. Cl.$^2$ ........................ B01J 23/78; B01J 23/80; B01J 23/84; B01J 23/86
[52] U.S. Cl. ...................................... 252/468; 252/470; 252/471; 252/473; 252/474; 585/661; 585/663
[58] Field of Search ............... 252/468, 470, 471, 473, 252/474

[56] References Cited

U.S. PATENT DOCUMENTS

| | | | |
|---|---|---|---|
| 3,084,125 | 4/1963 | Soderquist et al. ................. | 252/430 |
| 3,361,683 | 1/1968 | Gutmann ............................. | 252/470 |
| 3,577,354 | 5/1971 | Kehl .................................... | 252/468 |
| 3,595,810 | 7/1971 | Kehl .................................... | 252/468 |
| 3,843,745 | 10/1974 | Christman et al. .............. | 252/468 X |
| 3,849,339 | 11/1974 | Turley et al. .................... | 252/455 R |
| 4,052,338 | 10/1977 | Riesser ............................... | 252/470 |
| 4,098,723 | 7/1978 | Riesser ............................... | 252/474 |
| 4,143,083 | 3/1979 | Riesser ............................... | 252/470 |

*Primary Examiner*—W. J. Shine
*Attorney, Agent, or Firm*—Shell Oil Company

[57] ABSTRACT

Spinels promoted with an alkali metal oxide and vanadium oxide are useful catalysts for the dehydrogenation of hydrocarbons to the corresponding more unsaturated hydrocarbons and result in an improved catalyst.

10 Claims, No Drawings

4,220,560

SPINEL DEHYDROGENATION CATALYST

BACKGROUND OF THE INVENTION

1. Field of the Invention

This invention relates to improved catalysts for the dehydrogenation of hydrocarbons to corresponding more-unsaturated hydrocarbons, more particularly, to the production of vinyl aromatic hydrocarbons from alkyl aromatic hydrocarbons and to the production of olefins from the corresponding more-saturated aliphatic hydrocarbons.

2. The Prior Art

The vinyl benzenes and butadienes play a particularly important role in the preparation of synthetic rubbers, plastics and resins. The polymerization of styrene for example with various comonomers such as butadiene to produce synthetic rubbers is well known as is the polymerization of styrene to produce polystyrene resins.

Styrene and butadiene are typically produced from ethyl benzene and butylene, respectively, by dehydrogenation over solid catalysts in the presence of steam, and at temperatures ranging from 500° C. to 700° C. Spinels are known to dehydrogenation hydrocarbons. See for example, Kehl et al U.S. Pat. Nos. 3,577,354 issued May 4, 1971 and 3,595,810 issued July 27, 1971 which disclose the use of zinc chromium ferrite and magnesium chromium ferrite spinels as useful dehydrogenation catalysts. Potassium oxide is known as a promoter for spinels for non-oxidative dehydrogenation processes. See example 6 of U.S. Pat. No. 3,843,745 issued Oct. 22, 1974.

The traditional non-oxidative dehydrogenation catalyst is an iron oxide-potassium oxide-chromium oxide catalyst. This is not a spinel type of catalyst. Illustrative of the traditional type of catalyst is that of Turley et al, U.S. Pat. No. 3,849,339, issued Nov. 19, 1974. The addition of vanadium to the traditional catalysts is illustrated in U.S. Pat. Nos. 4,052,338 issued Oct. 4, 1977 to Riesser, in 3,361,683 issued Jan. 2, 1968 to Gutmann and in 3,084,125 issued Apr. 2, 1963 to Soderquist. The use of a spinel promoted with an alkali metal oxide and vanadium oxide allows the dehydrogenation process to operate at lower steam to hydrocarbon ratios than do traditional catalysts. Operation at lower steam to hydrocarbon ratios results in a considerable savings in energy per unit of dehydrogenated hydrocarbon produced.

SUMMARY OF THE INVENTION

Cobalt, zinc, manganese or magnesium chromium-ferrite spinels, when promoted an alkali metal oxide and vanadium oxide provide excellent catalysts for dehydrogenation processes. They are particularly useful for the preparation of a compound having the formula R—CH=CH$_2$ by non-oxidative dehydrogenation of a compound having the formula R—CH$_2$—CH$_3$, wherein R is a phenyl, alkyl or alkenyl group, carried out by passing a mixture of a compound having the formula R—CH$_2$—CH$_3$, wherein R is a phenyl, alkyl or alkenyl group, and superheated steam at the dehydrogenation temperature over said spinel catalyst containing an alkali metal oxide and vanadium oxide as promoters.

The promoted spinels of the instant invention are able to operate at lower steam to hydrocarbon ratios than traditional catalysts. In particular, the catalyst of the present invention is useful for converting ethylbenzene to styrene.

DESCRIPTION OF THE PREFERRED EMBODIMENTS

The invention may be defined as an improved process for the preparation of a compound having the formula R—CH=CH$_2$ by non-oxidative dehydrogenation of a compound having the formula R—CH$_2$—CH$_3$, wherein R is a phenyl, alkyl or alkenyl group, carried out by passing a mixture of a compound having the formula R—CH$_2$—CH$_3$, wherein R is a phenyl, alkyl or alkenyl group, and superheated steam at the dehydrogenation temperature over a spinel catalyst containing an alkali metal oxide and vanadium oxide as promoters. The invention also relates to the catalyst compositions. An additional advantage obtained by the use of this catalyst system is that less superheated steam is required than if the same catalyst is used without vanadium oxide as well as if a traditional catalyst is used. Particularly, for making styrene, the steam/ethyl benzene molar ratio will be between 6 and 12.

The group of compounds having the formula R—CH$_2$—CH$_3$ comprises the compounds to be dehydrogenated wherein R is a phenyl, alkyl or alkenyl radical. Special alkyl or alkenyl groups are those which contain from 2 to 20 carbon atoms, and they can have a straight-chain or a branched structure. Specific mention is made here of isoamylene, butylene and ethyl benzene.

The catalysts are generally spinels of the formula $A_aCr_bFe_cO_4$, wherein A is cobalt, zinc, manganese, or magnesium or mixtures thereof;
Cr, chromium; Fe, iron;
a is 1,
b is between 0 and 1,
c is between 1 and 2, and the sum of a+b+c is 3.

The preferred catalyst uses a spinel having the formula $A_aCr_bFe_cO_4$, wherein A is cobalt, zinc, manganese, or magnesium or mixtures thereof; Cr, chromium; Fe, iron;
a is 1,
b is from 0.05 to 1.0,
c is from 1.0 to 1.95 and the sum of a+b+c is 3.

In another catalyst, which is even more preferred, A is magnesium or manganese. In a given catalyst A may also be composed of two metals, such as cobalt and magnesium or magnesium and manganese, provided that the sum of their subvalues for a is 1.

The spinel catalyst must be activated by one or more alkali metal oxides, such as those of sodium, potassium or cesium, and by vanadium oxide. The catalyst generally contains from about 0.1 to about 20% by weight of alkali metal oxide and from about 0.1 to about 10% by weight of vanadium oxide based on the total weight of catalyst and promoters. Illustrative of spinels used to prepare the promoted catalysts of the instant invention are:

$MgCrFeO_4$, $MgFe_{1.5}Cr_{0.5}O_4$, $MnFe_{1.5}Cr_{0.5}O_4$, $MgFe_{1.75}Cr_{0.25}O_4$ and $MgFe_{1.9}Cr_{0.1}O_4$.

Spinel formation may be accomplished by reacting an active compound of iron with an active compound of the designated metals of the spinel. By active compound is meant a compound which is reactive under the conditions to form the spinel. Starting compounds if iron or the other metals may be such as the nitrates, hydroxides, hydrates oxalates, carbonates, acetates, formates, halides, oxides, etc. The starting compounds are suitably oxides on compounds which will decompose to oxides during the formation of the spinel such as organic and inorganic salts or hydroxides. For example, manganese carbonate may be reacted with iron and chromium oxide hydrates to form manganese chromium ferrite spinel. Salts of the desired metals may be coprecipitated such as disclosed in U.S. Pat. No. 3,450,787 and the precipitate heated to form the spinel. Desired spinels may be obtained by conducting the reaction to form the spinel at relatively low temperatures, that is, at temperature lower than some of the very high temperatures used for the formation of some of the semi-conductor applications. Good results, e.g., have been obtained by heating the ingredients to a temperature high enough to produce the required spinel but at conditions no more severe than equivalent to heating 950° or 1000° C. for 90 minutes in air and generally the maximum temperature will be less than 1300° C. and preferably less than 1150° C. Methods for preparing catalysts to be modified according to this invention are disclosed in U.S. Pat. Nos. 3,270,080; 3,284,536; 3,303,234-5; 3,303,238; 3,308,182; 3,334,152; 3,342,890 and 3,450,787 and these disclosures are hereby incorporated by reference. The catalysts may contain unreacted precursors of the spinel such as the oxides of A, Cr or iron. Preferred spinel forming temperatures range from about 700° to about 1000° C.

The catalyst promoters may be added to the catalyst at any stage of catalyst preparation. Generally the promoters will be added at such time that there will be intimate mixing with the other ingredients. The promoters may be added prior to or during spinel formation in which case the promoting elements may or may not become a part of the crystalline structure. However, it has been discovered that excellent catalysts are prepared when the promoters are added to the catalyst after spinel formation has begun or after spinel has been formed and this is a preferred embodiment of the invention.

The alkali metal promoter is added to the catalyst in various forms. For example, it may be added as the oxide, or as other compounds which are convertible, at least in part, under catalyst preparative conditions, to the oxides, such as the hydroxide, the carbonates, the bicarbonates, the phosphates, the borates, the acetates, and the like. Preferred alkali metal compounds are oxides and carbonates, particularly carbonates. The alkali metal compounds are conveniently measured as the oxides.

Vanadium is added to the catalyst as vanadium pentoxide or as salts or other compounds thermally decomposable under catalyst preparative conditions to the oxides, such as sulfates, oxysulfates, sulfides, or vanadates. The vanadium is present in the catalyst in one or mixtures of more than one of its possible oxidation states, the pentavalent state being the preferred state. The vanadium compound(s) is conveniently measured as the vanadium pentoxide.

When promoters are added to the catalyst after spinel formation, the catalyst will be calcined, when necessary to convert the promoter compounds to oxides. Calcination temperatures range from about 600° C. to about 1000° C.

The dehydrogenation reaction is usually carried out at reaction temperatures of about 500°–700° C. However, higher or lower temperatures may be used without departing from the scope of this invention. The use of atmospheric, sub-atmospheric, or super-atmospheric pressure is suitable. However, it is preferable to operate at as low a pressure as is feasible, and atmospheric or subatmospheric pressure is preferred. The process of the invention may be carried out in batch, semi-continuous, or continuous operation, with continuous operation being preferred. The catalyst is employed in the form of a fixed bed, or in fluidized or suspended form. It is preferable to utilize a fixed bed. The reaction may be carried out in single stage reactors or by staging in series reactors. The reactors may be of various designs, e.g., downflow reactors, radial reactors, etc.

With the use of the catalyst of this invention, it is desirable to add steam to the reactant feed to aid in the removal of carbonaceous residues from the catalyst. The reaction feed contains from 2–30 moles of steam for every mole of feed. Catalysts having higher potassium contents are usually employed at lower feed to steam ratios. Feed to steam ratios of from about 1:6 to about 1:18 are desirable. Good results are obtained with feed to steam ratios of about 1:9 to about 1:12.

The contact time of the reactant gas with the catalyst is usually defined in terms of gaseous-hourly-space velocity (volumes of hydrocarbon reactant per volume of catalyst per hour, i.e., GHSV). The GHSV according to this invention may vary from about 10 to 3000 and is preferably adjusted within this range to effect the degree of conversion desired for the particular feed in question.

The preparation of catalysts, according to the invention, and their use will be further described by the following illustrative embodiments which are provided for illustration and are not to be construed as limiting the invention.

EXAMPLE 1: Catalyst Preparation 38.3 Grams (g) of $Fe(NO_3)_3.9H_2O$, 128.6 g of $Mg(NO_3)_2.6H_2O$ and 20 g of $Cr(NO_3)_3.9H_2O$ were mixed and the mixture was gradually heated to 800° C. during 22 hours and calcined for 2 hours at 800° C. The nitrates were thus dissociated and 100 g of a magnesium ferrochromite ($MgFe_{1.9}Cr_{0.1}O_4$) were obtained.

85 G of the said ferrochromite, 3.86 g of $NH_4VO_3$ and 3.8 g of potassium alginate were mixed and the resultant mixture was impregnated with an aqueous solution composed of 16.4 g of $K_2CO_3$, 0.64 g of sorbitol and 22 cc of $H_2O$. The total mixture was thoroughly mixed and the paste was extruded and pelletized. The pellets were dried for 12 hours at 120° C., and calcined for 2 hours at 800° C.

The catalyst contained 85% by weight of $MgFe_{1.9}Cr_{0.1}O_4$, 12% by weight of $K_2O$ and 3% by weight of $V_2O_5$. This catalyst was used in Example 2 below.

The above was repeated except the $NH_4VO_3$ was not utilized. The catalyst contained 88% by weight of $MgFe_{1.9}Cr_{0.1}O_4$ and 12% by weight of $K_2O$. This catalyst was used in Example 2 below.

EXAMPLE 2

For the preparation of styrene the steam and ethyl benzene was mixed and heated to 400° C., and then introduced into the reactor.

The following conditions were utilized:
volume of the catalyst bed, in ml: 100
size of the catalyst, in mm: 2.8 to 3.2
purity of the ethyl benzene, in %: 99
di-ionized water for the production of steam, temperature in °C.: 550 to 650
pressure, in bars: 1
molar ratio $H_2O$:ethyl benzene: 12
space velocity, in l/lh: 0.65.

The reaction product was then cooled and the quantity of styrene determined by chromatography.

The selectivity is defined as follows:

$$\% \text{Sel}_{(quantity)} = 100 \frac{\text{quantity of styrene}}{\text{total quantity of hydrocarbons} - \text{quantity of unconverted ethyl benzene}}$$

Table I states the selectivity and activity levels of a catalyst according to the invention and a catalyst of the same composition except that vanadium oxide is not present as a promoter (so that it is not a catalyst according to the invention).

Table I

| Catalyst | Comp. | Temperature at 70% conversion after a 17-day test, °C. | Selectivity at 70% conversion after a 17-day test, % |
|---|---|---|---|
| MgFe$_{1.9}$Cr$_{0.1}$O$_4$ + K$_2$O | Bal. 12% | 594 | 89.5 |
| MgFe$_{1.9}$Cr$_{0.1}$O$_4$ + K$_2$O + V$_2$O$_5$ | Bal. 12% 3% | 595 | 94.5 |
| MnFe$_{1.5}$Cr$_{0.5}$O$_4$ + K$_2$O | Bal. 12% | 598 | 89.5 |
| MnFe$_{1.5}$Cr$_{0.5}$O$_4$ + K$_2$O + V$_2$O$_5$ | Bal. 12% 3% | 618 | 95.0 |

EXAMPLE 3

Styrene was prepared from ethyl benzene under the same reaction conditions as those of Example 2, except that the molar ratio H$_2$O:ethyl benzene and the reaction time was varied. Table II states the selectivity and activity levels of two catalysts according to the invention as well as a reference catalyst.

Table II

| Catalyst | Weight Per 100 cm$^3$ g | Molar Ratio H$_2$O/EB = 12 | | |
|---|---|---|---|---|
| | | T(70) °C. | S(70) °C. | Test Duration h |
| Shell 005* | 153 | 603 | 94.5 | 170 |
| Reference Catalyst | 153 | 606 | 94.5 | 340 |
| MgFe$_{1.9}$Cr$_{0.1}$O$_4$ + 12% K$_2$O + 3% V$_2$O$_5$ | 141 141 | 597 | 94.5 | 170 |
| -d°- | 108 | 613 | 94.5 | 150 |
| -d°- | 134 | 606 | 94.5 | 100 |
| MnFe$_{1.5}$Cr$_{0.5}$O$_5$ + 12% K$_2$O + 3% V$_2$O$_5$ | 146 146 146 | 618 618 618 | 95.0 95.0 95.0 | 100 150 340 |

| Catalyst | Molar Ratio H$_2$O/EB = 9 | | | Molar Ratio H$_2$O/EB = 6 | | |
|---|---|---|---|---|---|---|
| | T(70) °C. | S(70) % | Test Duration h | T(40) °C. | S(40) % | Test Duration h |
| Shell 005* Reference catalyst | Continuous Deactivation | — | — | — | — | — |
| MgFe$_{1.9}$Cr$_{0.1}$O$_4$ + 12% K$_2$O + 3% V$_2$O$_5$ | 624 624 | 94.5 94.5 | 50 290 | — — | — — | — — |
| -d°- | 622 | 94.5 | 340 | 629 | 95 | 170 |
| -d°- | 616 | 94.5 | 50 | — | — | — |
| MnFe$_{1.5}$Cr$_{0.5}$O$_4$ + 12% K$_2$O + 3% V$_2$O$_5$ | 620 622 | 94.5 94.5 | 50 220 | — — | — — | — — |

*Shell 005 is a conventional catalyst, commercially available, containing Fe$_2$O$_3$-2.45% w Cr$_2$O$_3$-12.6% w K$_2$O-3.0% w V$_2$O$_5$-1.6% w CoO.

What is claimed is:

1. A catalyst for the dehydrogenation of hydrocarbons to a more unsaturated hydrocarbon comprising:
   (a) a spinel having the formula:

$$A_aCr_bFe_cO_4$$

wherein, A is selected from the group consisting of cobalt, zinc, manganese, magnesium or mixtures thereof, a is 1, b is between 0 and 1, c is between 1 and 2 and the sum of a+b+c is 3,
   (b) from about 0.1 to about 20 percent by weight of an alkali metal oxide, and
   (c) from about 0.1 to about 10 percent by weight of a vanadium oxide.

2. The catalyst of claim 1 wherein alkali metal oxide is sodium, potassium or cesium oxide.

3. The catalyst of claim 2 wherein the alkali metal oxide is potassium oxide.

4. The catalyst of claim 1, 2 or 3 wherein A is magnesium or manganese.

5. The catalyst of claim 1 wherein in the formula A$_a$Cr$_b$Fe$_c$O$_4$, b is 0.05 to 1.0 and c is from 1.0 to 1.95.

6. The catalyst of claim 5 wherein the alkali metal oxide is sodium, potassium or cesium oxide.

7. The catalyst of claim 6 wherein the alkali metal oxide is potassium oxide.

8. The catalyst of claim 5, 6 or 7 wherein A is magnesium or manganese.

9. The catalyst of claim 1 wherein the hydrocarbon is butylene and the more unsaturated hydrocarbon is butadiene.

10. The catalyst of claim 1 wherein the hydrocarbon is ethyl benzene and the more unsaturated hydrocarbon is styrene.

* * * * *